United States Patent [19]

Vora

[11] Patent Number: 4,575,567

[45] Date of Patent: * Mar. 11, 1986

[54] ADSORBENT REGENERATION IN ETHERIFICATION PROCESSES

[75] Inventor: Bipin V. Vora, Elk Grove Village, Ill.

[73] Assignee: UOP Inc., Des Plaines, Ill.

[*] Notice: The portion of the term of this patent subsequent to May 8, 2001 has been disclaimed.

[21] Appl. No.: 636,900

[22] Filed: Aug. 2, 1984

Related U.S. Application Data

[63] Continuation-in-part of Ser. No. 598,122, Apr. 9, 1984, which is a continuation-in-part of Ser. No. 395,413, Jul. 6, 1982, Pat. No. 4,447,653.

[51] Int. Cl.$^4$ .................... C07C 41/06; C07C 41/00
[52] U.S. Cl. .................... 568/697; 568/699; 585/331; 585/709; 585/723
[58] Field of Search ............ 568/697, 699; 585/331, 585/709, 723

[56] References Cited

U.S. PATENT DOCUMENTS

| | | | |
|---|---|---|---|
| 3,726,942 | 4/1973 | Louder | 568/697 |
| 4,322,565 | 3/1982 | Dotson et al. | 568/697 |
| 4,371,718 | 2/1983 | Hutson | 568/697 |
| 4,409,421 | 10/1983 | Herwig | 568/697 |
| 4,447,653 | 5/1984 | Vora | 568/697 |

*Primary Examiner*—Howard T. Mars
*Attorney, Agent, or Firm*—Thomas K. McBride; William H. Page, II; John F. Spears, Jr.

[57] ABSTRACT

An improved method is disclosed for regenerating adsorbents used in an integrated process for the production of ethers such as methyl tertiary butyl ether by the reaction of an alcohol with an isoolefin. The sorbents are used to remove oxygenated compounds such as the product ether and the feed alcohol from a hydrocarbon-rich stream withdrawn from the etherification zone. The regeneration procedure includes contacting the sorbent with a heated hydrocarbon stream. The resultant contaminated hydrocarbon stream is passed into a stripping column used to remove light ends from the effluent of a dehydrogenation zone in which the isoolefin fed to the etherification zone is produced. The oxygenated compounds collected on the sorbent are thus selectively recycled or rejected rather than being destroyed or lost in low purity effluent streams.

7 Claims, 1 Drawing Figure

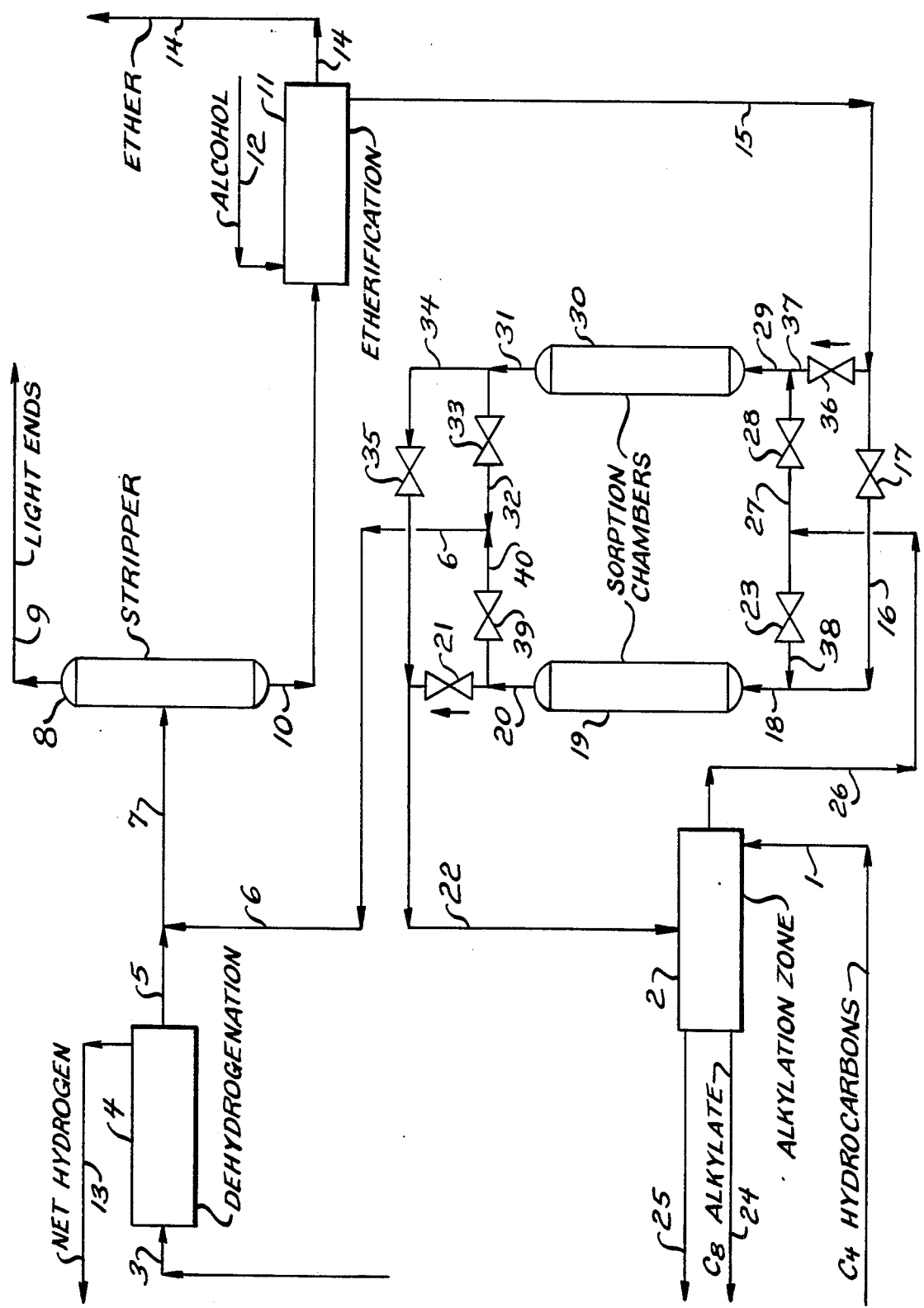

ADSORBENT REGENERATION IN ETHERIFICATION PROCESSES

CROSS REFERENCE TO RELATED APPLICATIONS

This application is a continuation-in-part of my prior copending application Ser. No. 598,122 filed on Apr. 9, 1984 which was a continuation-in-part of application Ser. No. 395,413 filed on July 6, 1982, now U.S. Pat. No. 4,447,653. The teachings of these prior applications is expressly incorporated herein.

FIELD OF THE INVENTION

The invention relates to an integrated process for the production of ethers by the reaction of an alcohol with an isoolefin. The invention more directly relates to such an integrated process wherein methyl tertiary butyl ether is produced by the reaction of methanol and isobutylene, with the isobutylene being produced in a dehydrogenation zone within the process. The invention specifically relates to the regeneration of solid sorbents used to selectively remove oxygen-containing compounds and possibly other undesired compounds from a $C_4$ hydrocarbon stream removed from an etherification process.

INFORMATION DISCLOSURE

The production of ethers by the reaction of an isoolefin with an alcohol is well known and is practiced commercially. This highly selective reaction is also used to remove isoolefins, especially isobutylene, from mixed hydrocarbon streams such as the $C_4$ streams produced in an ethyleneproducing steam cracking plant or in an FCC unit. Increased attention has been recently focused on ether production due to the rapidly increasing demand for lead-free octane boosters for gasoline such as methyl tertiary butyl ether (MTBE).

A detailed description of processes, including catalysts, processing conditions and product recovery, for the production of MTBE from isobutylene and methanol are provided in U.S. Pat. Nos. 2,720,547 and 4,219,678 and in an article at page 35 of the June 25, 1979 edition of *Chemical and Engineering News*. The preferred etherification zone is described in a paper presented at the American Institute of Chemical Engineers 85th National meeting on June 4–8, 1978 by F. Obenaus et al.

Descriptions of integrated processes for producing MTBE, including those which utilize butane isomerization and/or butane dehydrogenation, are found in U.S. Pat. Nos. 3,726,942; 4,118,425; 4,252,541; and 4,329,516. The last of these references is believed the most pertinent to this application because of the arrangement of the process steps and the similar operation of the various process steps. FIG. 6 of an article at page 191 of the Nov. 10, 1980 edition of *The Oil and Gas Journal* is also pertinent since it presents an integrated process for producing MTBE from mixed butanes having a flow similar to that shown in the subject Drawing. The flow paths of many process streams are the same in this reference and in the preferred embodiment of the subject process. One exception is that a normal butylene hydrogenation zone is shown in place of the adsorption zone used in the subject process. In addition no regeneration streams are shown in this reference, and the treated stream is not passed into an alkylation zone.

It is also well known to use a solid adsorbent, such as alumina or zeolitic materials, to treat liquid phase hydrocarbon process streams for the removal of small quantities of undesired contaminants. These adsorbents have been used to remove water, sulfur compounds and various hydrocarbonaceous compounds including such oxygenated compounds as alcohols from process streams. This use of adsorbents is taught in U.S. Pat. Nos. 2,943,105; 3,489,808; 3,931,350; and 4,098,684.

Previously cited U.S. Pat. No. 3,726,942 discloses removing methanol from the unreacted hydrocarbons withdrawn from an MTBE reaction zone through the use of molecular sieves. U.S. Pat. No. 4,322,565 teaches the removal of alcohols from the effluent of an etherification reaction zone through absorption of the alcohol on solid calcium chloride. The reference is also pertinent for teaching that the absorbent can be regenerated with a hot hydrocarbon stream which can be charged to the etherification reactor to recycle the alcohol. This absorption step is a bulk removal which replaces fractional distillation of the etherification reaction zone effluent.

U.S. Pat. No. 4,371,718 is pertinent for its teaching, as shown on the drawing, that the effluent of the MTBE reactor may be fractionated to yield a $C_4$ stream which is then passed through methanol adsorption zones. The adsorption zones are regenerated with hot hydrocarbons which are then passed into the MTBE reactor. The methanol-free $C_4$ stream is then passed into an alkylation zone.

BRIEF SUMMARY OF THE INVENTION

The invention provides a method of regenerating solid sorbents used to remove oxygenates from a process stream of an integrated etherification process. The method comprises contacting the used sorbent with a high temperature stream comprising a hydrocarbon present in the process and then passing the regenerent stream directly into a dehydrogenation unit stripping column located upstream of the etherification unit. The feed alcohol and product ether of the process present in the regenerent stream are concentrated into the bottoms stream of the stripping column, which is passed into the etherification zone. These valuable compounds are thereby recycled for eventual recovery in a closed loop system. Simultaneously the stripping column rejects light oxygen-containing by-products produced in the etherification reactor as an overhead stream, which also contains by-products of the dehydrogenation unit.

The invention may be characterized as a process for the production of an ether which comprises the steps of passing a first process stream comprising a feed isoparaffin through a catalytic dehydrogenation zone and thereby producing a reaction zone effluent stream comprising the isoparaffin and a corresponding isoolefin; passing the reaction zone effluent stream and a hereinafter characterized second process stream into a stripping column and producing a stripping column bottoms stream comprising the isoparaffin, the isoolefin and oxygen-containing hydrocarbonaceous compounds; passing the stripping column bottoms stream and an alcohol feed stream into an etherification zone, and withdrawing from the etherification zone a product stream comprising the ether and a $C_4$ hydrocarbon-rich third process stream comprising the isoparaffin and oxygen-containing hydrocarbonaceous compounds; removing oxygen-containing hydrocarbonaceous compounds from the hydrocarbonaceous third process stream by contacting the third process stream with a selective sorbent at sorption-promoting conditions in a sorption zone and thereby producing a treated process stream which comprises the isoparaffin and is substantially free of oxygen-containing hydrocarbonaceous compounds; removing at least a first portion of the treated process stream from the process; regenerating sorbent in the sorption zone by a regeneration procedure which comprises contacting sorbent present in the sorption zone with a regeneration stream comprising a regenerent hydrocarbon having the same number of carbon atoms per molecule as the feed isoparaffin at regeneration-promoting conditions to produce the previously referred to second process stream, which comprises the feed isoparaffin and oxygencontaining hydrocarbonaceous compounds.

BRIEF DESCRIPTION OF THE DRAWING

The Drawing illustrates the overall flow of an integrated process for producing ethers in which the preferred embodiment of the inventive concept is employed in the regeneration of the sorbent used to treat the hydrocarbon stream flowing through lines 15 and 22. The dehydrogenation reactor effluent stream comprising isobutane, isobutylene, normal butane and butenes is combined with a regenerent stream carried by line 6 and passed into a stripping column 8 via line 7. The light ends present in the admixture of these two streams, such as ethane and dimethyl ether, are removed from the process in line 9 as the net overhead stream of the stripping column. The net bottoms stream of the stripping column, which contains C4 hydrocarbons and the less volatile oxygenates present in the regenerent stream, is passed into the etherification zone 11 through line 10. The isobutylene fed to this zone reacts with the alcohol charged to the process through line 12 to produce an ether which is withdrawn from the process as the product stream of line 14.

A C4 hydrocarbon-rich process stream is withdrawn from the etherification zone via line 15 and passed through the adsorption chamber 19 of a multi-chamber adsorption zone. The adsorbent selectively removes the small amounts of the product ether, feed alcohol and other oxygenates present in the C4-rich stream. The resultant treated process stream is then passed into a downstream process unit such as an alkylation zone 2 via line 22. A heated regenerent stream from the alkylation zone is passed through a second adsorption chamber 30 as part of the regeneration procedure for the adsorbent present within this chamber. This regenerent stream removes oxygenates from the adsorbent, and the regenerent stream then carries the oxygenates into column 8 via lines 32 and 6. The use and regeneration of the chambers is periodically alternated to provide continuous operation.

DETAILED DESCRIPTION

Etherification processes have been constructed and proposed for the production of a variety of ethers. These ethers are themselves useful end products and can be used as feed compounds in processes for producing other valuable chemical compounds. For instance, plans have been announced to produce pure isobutane for the manufacture of polyisobutylenes and tertbutylphenol by first producing methyl tertiary butyl ether (MTBE) and then cracking the MTBE to yield isobutylene and methanol which is recycled. Large amounts of MTBE are also being produced for use as anti-knock compounds in lead-free gasoline. Etherification processes therefore find utility in both the petrochemical and petroleum refining industries.

The majority of the description of the invention is presented in terms of the reaction of isobutylene with methanol to form MTBE since these are the preferred feed materials and the commercially predominant reaction. However, it is not intended to thereby lessen the scope of the inventive concept, which may be applied in the production of other ethers when a similar hydrocarbon-rich etherification zone effluent stream and stripping column are present in the process. The inventive concept may therefore be applied in general to the reaction of isoolefins having less than six carbon atoms per molecule with water-soluble alcohols which preferably have less than four carbon atoms per molecule. The next preferred alcohol after methanol is ethanol but other alcohols such as propanols, ethylene glycol or propylene glycol can also be consumed in the process. The isoolefin is preferably derived by dehydrogenation of isobutane or isopentane. The subject process may therefore be employed in the production of a wide variety of ethers other than MTBE including methyl tertiary amyl ether, ethyl tertiary amyl ether, and ethyl tertiary butyl ether.

The ethers are produced by the reaction of the alcohol and the isoolefin in an etherification zone. The ethers are then separated from unreacted hydrocarbons, water and unreacted alcohol to yield the ether product stream. In the case of MTBE production, the unreacted hydrocarbons include normal butenes, formed from normal butane which enters the dehydrogenation zone, and possibly various butadienes also formed in the dehydrogenation zone since these compounds do not react with the alcohol. Also normally present is a larger amount of isobutane remaining from the isobutane present in the dehydrogenation zone feed stream which was not dehydrogenated. These unreacted hydrocarbons are withdrawn from the separatory facilities used to recover the ether as a separate hydrocarbonaceous effluent stream, which is also referred to herein as the third process stream.

In the integrated processes to which the subject invention is directed, this hydrocarbonaceous effluent stream may be recycled to produce more of the isoolefin, normally by the sequential steps of isomerization and dehydrogenation, and is then referred to as the hydrocarbon recycle stream. The terms "recycle stream" and "hydrocarbonaceous effluent stream" are therefore used interchangeably herein depending on the configuration of the process. If not removed from the process, the normal butenes and any butadienes present in the recycle stream will accumulate within the process and cause the hydrocarbon recycle stream to increase in volume. The presence of these compounds also has detrimental effects on the preferred dehydrogenation catalyst. Other components of the hydrocarbon recycle stream include smaller amounts of various oxygenates such as the product ether, the feed alcohol and oxygen-containing reaction by-products, such as dimethyl ether, resulting from side reactions. It is also not desirable to pass these oxygenates into isomerization of dehydrogenation zones because of their effects on the preferred catalysts. It is threfore desirable to remove, alter or destroy all of these undesired compounds before the hydrocarbon recycle stream is passed into an isomerization or dehydrogenation zone.

It is also desirable to remove the various oxygen-containing hydrocarbonaceous compounds, referred to herein as oxygenates, from the hydrocarbonaceous effluent stream in instances other than the production of additional isoolefin by isomerization and dehydrogenation. For instance, it may be desired to purify the effluent stream prior to its use in an oligomerization process. It may also be desired to consume the normal olefins present in the effluent stream in a catalytic condensation zone or to feed the effluent stream into a process for the selective recovery of normal olefins by adsorption. In these instances the hydrocarbonaceous effluent stream recovered from the etherification zone is removed from the process.

In a limited embodiment of the subject invention, the hydrocarbonrich effluent stream is passed into an HF alkylation zone for the production of $C_8$ alkylate by the reaction of normal butenes with isobutane. This process is described in detail below. It is undesirable to pass methanol into an HF alkylation zone since it accumulates in the HF and is very difficult to remove from the process. It is also undesirable to allow light oxygenates such as dimethyl ether (DME) to enter an HF alkylation zone. DME is essentially a noncondensable material at the conditions maintained in the alkylation zone. It must therefore be removed by venting HF vapor to an off-gas scrubbing zone. This is an inherently dangerous and costly procedure, which generates hazardous waste disposal problems.

Heretofore it has been suggested to remove undesired compounds from the hydrocarbon recycle stream by hydrotreating. That is, the olefins, diolefins and oxygenates were hydrogenated to form paraffins. Hydrotreating the hydrocarbon recycle stream can add considerably to the capital and operating costs of the overall process. It has recently been found that solid sorbents may be used to remove the undesired compounds from the recycle or hydrocarbonaceous effluent stream and that these sorbents may be regenerated. However, these prior art regeneration methods do not reject byproduct oxygenates while recovering the feed alcohol or the product ether. It is an objective of the subject invention to provide an improved etherification process employing sorbents to remove oxygenates from the hydrocarbon stream separated from the etherification reactor effluent. It is a further objective of the subject invention to reduce the cost and difficulty of regenerating sorbents used to remove oxygenates from the hydrocarbon effluent stream of integrated etherification processes. It is another objective of the subject invention to provide an economical method of recovering desired oxygenated hydrocarbonaceous compounds, such as product MTBE, present in the $C_4$ hydrocarbon recycle stream of an integrated process for producing MTBE while rejecting undesired oxygenates.

In the subject process oxygen-containing hydrocarbonaceous compounds, and possibly other compounds as described below, are removed from the hydrocarbonaceous effluent stream by contacting the effluent stream with a sorbent solid. The sorbent, which may function as a physical or as a chemical adsorbent, is preferably disposed as a fixed bed in two or more cylindrical contacting chambers. The flow of the recycle stream is preferably switched between different chambers to allow continuous processing of the recycle stream while the sorbent in the chambers which are not being used is either regenerated or replaced depending on the regenerability and remaining capacity of the sorbent. The sorbent may also be contained in a different chamber configuration such as a moving bed or a fluidized bed.

The required sorption-promoting conditions will depend on such factors as the specific sorbent used in the process and the chemical compounds to be removed from the recycle stream. A general range of suitable sorptionpromoting conditions includes a superatmospheric pressure less than about 500 psig, although higher pressures may be employed, and a temperature less than about 160° F. (71° C.). A liquid hourly space velocity of less than 10 hr.$^{-1}$ should be employed. A preferred range of sorption-promoting conditions includes a pressure between 10 and about 200 psig, a temperature between 50° and 150° F. (10° and 65° C.) and a liquid hourly space velocity between 0.3 and 3.0 hr.$^{-1}$.

The sorbent is preferably in the form of solid spherical particles on the order of about 1/16 to ¼ of an inch in diameter. The preferred sorbents are the zeolitic materials known as molecular sieves and ion exchange resins. The selection of sorbents for use in the subject process is dependent on the effectiveness, selectivity and regenerability of the particular solid and is not dependent on the manner in which the sorbent acts to remove the undesired compounds. The sorbent may therefore act by physical or chemical adsorption or by ion exchange. As is known to those skilled in the art, these materials are normally selective as to the compounds they tend to sorb, and it is therefore necessary to carefully select the proper materials. Small scale testing may be required in some instances as part of the selection process to determine the appropriateness of materials other than those listed herein. It is contemplated that the solid sorbent may also be chosen from the group consisting of natural and synthetic aluminas, clays, charcoals and other known sorbents. The preferred sorbents are type 5A and type 13X molecular sieves which should remove both the oxygen-containing impurities and any sulfur compounds such as dimethylsulfoxide which may be present due to the admixture of a feed stream with the hydrocarbonaceous effluent stream. A type 3A molecular sieve may be employed to remove water from the recycle hydrocarbon stream. The terms "sorbent" and "adsorbent" and the terms "sorption" and "adsorption" are used interchangeably herein.

The regeneration of the sorbents may include a low temperature hydrogen stripping step in which the temperature of the hydrogen stream is gradually increased. The hydrogen regeneration gas stream preferably contains at least 85 mole percent hydrogen and has an initial temperature below 200° F. (93° C.). The temperature of the gas stream is gradually increased at a rate less than about 50 Fahrenheit degrees per hour until a temperature is reached in the range of about 300°–600° F. (149°–315° C.). Heated hydrocarbons can then be employed if desired to reach higher regeneration temperatures. This procedure is desired to ensure regeneration in the presence of olefins and diolefins on the sorbent. It is also possible that the low temperature hydrogen stripping step may not be required and that a conventional regeneration procedures such as pressure reduction and/or initial high temperature hydrocarbon, steam or nitrogen purging may be employed. The preferred "swing bed" regeneration of the sorbent includes contacting a contaminated off-stream bed of the sorbent with a heated portion of previously treated hydrocarbon recycle stream or other regenerent hydrocarbon. This stream should have a temperature above 250° F. (121° C.) and preferably above 300° F. (149° C.). Regeneration conditions also include a superatmospheric pressure preferably less than 250 psig. Another preferred source of the regenerent hydrocarbon is the stabilizer of an isomerization zone if one is present in the process. This is especially true when a sorptive treating step requiring the use of hot regenerent is also performed in the isomerization zone. Common regenerent preparation facilities can then be employed to service both hydrocarbon conversion zones. Other regenerent sources are described below.

The preferred regeneration media is a heated liquid phase stream. Alternatively the regeneration media may be a vapor phase stream. It is preferred that the oxygenate-containing regenerent liquid is passed into the stripping column by admixture with the dehydrogenation reaction zone effluent stream. However, the regenerent may if desired be passed separately into the stripping column. The passage of the regenerent into the stripping column allows the rejection of more volatile impurities such as dimethyl ether as part of the overhead stream of the stripping column. The same stripping column is therefore employed to reject light by-products of two different conversion zones, the etherification zone and the dehydrogenation zone.

The classification of chemical compounds present in the hydrocarbonaceous effluent stream as undesired compounds or as impurities will depend on such factors as the identity of the reacting alcohol and isoolefin and the susceptibility of the downstream catalyst(s) to poisoning or deactivation by the various compounds. Some of the compounds which it is desired to remove may be derived from a hydrocarbon feed stream if the feed stream is admixed into the recycle stream upstream of the sorption zone. However, it is believed that most or all of the compounds which it is desired to remove from the hydrocarbon recycle stream will normally be present in the recycle stream as it leaves the etherification zone. These compounds include the product ether, the feed alcohol and oxygen-containing reaction by-products. In the case of MTBE production, these compounds are MTBE, methanol and by-products including dimethyl ether and tertiary butyl alcohol. Up to 90 percent of the total oxygenates will be dimethyl ether.

Since the hydrocarbonaceous effluent stream is normally water washed to remove the vast majority of the water-soluble alcohols such as methanol, the effluent stream will contain water and most probably will be saturated with water. This water may also be removed from the effluent stream, if desired, by the sorbent. The hydrocarbon effluent stream will also contain mono- and diolefins produced in the dehydrogenation zone. In the preferred embodiment, these olefins are isobutylene and normal butylene and butadienes. It is preferred that most of the olefinic hydrocarbons present in the hydrocarbonaceous effluent stream are not removed during contact with the sorbent. Therefore, preferably less than 5 mole percent of any butadiene present in the effluent stream is removed from the effluent stream by contact with the solid sorbent. The thus-treated hydrocarbon stream is then passed into a deisobutanizer or other appropriate facility. If the normal butane content of the hydrocarbon stream is very low, it can be passed directly into the dehydrogenation zone.

The removal of oxygen-containing compounds from the hydrocarbonaceous effluent stream may by itself be sufficient to eliminate any requirement for subsequently hydrotreating the effluent stream. This assumes that the olefinic components are at a level which is tolerable in downstream portions of the process either due to a very low concentration of the olefinic compounds in the treated hydrocarbon stream or the ability of the catalysts to function properly with feed streams containing such mono- and diolefins. The characteristics of the dehydrogenation catalysts will therefore be very significant in determining the need for any further treatment for the effluent stream since the dehydrogenation catalyst's tendency to produce diolefinic hydrocarbons largely determines the concentration of diolefins in the effluent stream.

In the preferred form of the overall integrated etherification process, the net effluent stream of the dehydrogenation reaction zone, which comprises a mixture of olefins and saturated hydrocarbons, is fed to an etherification zone together with the feed alcohol. The etherification zone may take many different forms but is preferably similar to that described in U.S. Pat. No. 4,219,678 and shown in the previously cited paper. In this instance the isobutane or other isoolefin, methanol or other feed alcohol, and a recycle stream containing the product ether, and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

It is preferred that the effluent of the etherification reaction zone is passed into an intermediate point of a first fractionation column designed and operated to concentrate unconverted isoolefins and similar hydrocarbons present in the effluent into a net overhead stream. In the case of isobutene being the isoolefin, this column is a deisobutanizer. The net overhead stream of this column becomes the hydrocarbonaceous effluent stream of the subject process and is passed into the sorption zone, preferably after passage through a water wash zone to recover most of the methanol or other alcohol present in this stream. This overhead stream is also referred to herein as the third process stream. In those limited embodiments in which additional isoolefin is produced in the hydrocarbonaceous effluent stream is referred to as the recycle stream. The bottoms stream of the column receiving the reactor effluent contains most of the product ether and excess alcohol present in the reaction zone effluent stream and is passed into a second fractionation column. By proper operation of the second column, the entering materials may be separated into a second net overhead stream which is an alcohol-ether azeotrope and a second bottoms stream comprising relatively pure product ether which is withdrawn as the product stream of the process. The alcoholether azeotrope is preferably recycled to the beginning of the reaction zone. Further details on the separatory method and other aspects of the etherification zone may be obtained from the previously cited references.

After the hydrocarbonaceous stream has passed through the sorption zone, the resultant treated stream may be passed into a number of downstream processing units including polymerization or alkylation units. The treated stream may also be processed for the production of more of the isoolefin. The treated stream can therefore be recycled directly to the dehydrogenation zone. However, it is preferred to produce more isoolefin by first passing the recycle stream into a fractionation section of a fractionation and isomerization zone. Preferably this fractionation section comprises a single fractionation column but two or more columns could be employed if desired. This column is normally referred to as a deisobutanizer. The treated recycle stream should enter the column at an upper intermediate point. The isoparaffin component of the recycle stream and other streams entering the deisobutanizer becomes concentrated into the net overhead stream of the column and is passed into the dehydrogenation zone. Normal paraffins are removed from the column as part of a lower sidecut stream, which is preferably passed into the paraffin isomerization unit. The overhead stream of the column should be rich in the isoparaffin and the sidecut stream should be rich in the normal paraffin. In this embodiment the isobutane-rich overhead stream of the deisobutanizer would be passed into the butane dehydrogenation reaction zone. As used herein the term "rich" is intended to indicate that the process stream contains at least 55 mole percent of the particular chemical compound or class of compounds which is specified.

The regenerent hydrocarbon which is used to remove oxygenates from used adsorbent can be obtained from a number of sources. The source of the regenerent hydrocarbon in any particular situation will often be determined by the availability of suitable regenerent hydrocarbons from other processing units. It is highly preferred that facilities used to produce hot regenerent hydrocarbons for use in another process unit, such as an isomerization or alkylation unit, are also employed to produce the regenerent hydrocarbons for the subject process. This naturally reduces the costs of providing the regenerent. The dual use of the regenerent heaters and pumps of one unit is limited to situations in which the regenerent hydrocarbon is suitable for use in regenerating the adsorbent in both process units. During the production of MTBE in the subject process suitable regenerent hydrocarbons are normal butane and isobutane. In general the regenerent hydrocarbon should have the same number of carbon atoms per molecule as the feed isoparaffin charged to the dehydrogenation zone.

The Drawing illustrates the use of regenerent prepared in a motor fuel alkylation zone 2 to regenerate the adsorbent in chambers 19 and 30 of the subject process. In this process flow isobutane-rich hydrocarbons from line 1 enter the alkylation zone and are reacted with normal butanes in the etherification zone $C_4$ raffinate carried by line 22. This produces a high octane $C_8$ alkylate removed in line 24. Alkylation by-products, such as propane, and any other undesired compounds are rejected via line 25. Adsorption zones are customarily employed within the alkylation zone to dry the hydrocarbon stream of line 1.

A butane feed stream comprising isobutane and normal butane enters the dehydrogenation zone 4 via line 3. The isobutane stream is therein contacted with a dehydrogenation catalyst at dehydrogenation conditions to produce hydrogen removed through line 13 and a dehydrogenation reactor effluent comprising isobutane, isobutylene, normal butane and butenes carried by line 5. This effluent and the regenerent stream, which comprises recovered oxygenates and $C_4$ hydrocarbons, is passed into the stripper 8. Any MTBE and $C_4$ boiling range oxygenates present in the regenerent stream of line 6 together with the entering $C_4$ hydrocarbons from line 5 flow through line 10 to the etherification zone. The alcohol from line 12 reacts with the isobutylene to produce MTBE withdrawn in line 14. The remaining unreacted $C_4$ hydrocarbons are withdrawn as the $C_4$ raffinate stream carried by line 15. This stream passes through valve 36 in line 37 and through line 29 into the adsorption chamber 30 wherein it is contacted with an adsorbent which selectively retains the oygenates present in the untreated raffinate stream. The thus treated $C_4$ raffinate stream then flows through line 31 and open valve 35 in line 34 before passing into the alkylation zone via line 22. During the use of adsorbent chamber 30, valve 17 in line 16, valve 28 in line 27 and valve 33 in line 32 are closed.

The adsorbent in chamber 19 is being regenerated while the adsorbent in chamber 30 is treating the raffinate stream. The regenerating media is prepared and heated as required in the alkylation zone 2. The regenerent $C_4$ hydrocarbons, normal butane or isobutane or a mixture of both, is then passed through line 26, open valve 23 in line 38 and line 18 into the adsorbent chamber 19. The regenerent stream removes accumulated oxygenates from the adsorbent producing a stream comprising the regenerent $C_4$ hydrocarbons and oxygenates which flows through line 20 and open valve 39 in line 40 into line 6 for passage into the stripping column. Valve 21 is closed during the regeneration of chamber 19. When the regeneration cycle is switched to chamber 30 the various valves are opened or shut as required to isolate the flow streams.

The dehydrogenation zone employed in the process will contain a reaction zone and associated auxiliary process equipment such as condensers and a vapor-liquid separator which receives the partially condensed reactor effluent stream. A hydrogen-rich gas stream is preferably separated from the liquid condensed from the reactor effluent. A portion of this gas will normally be recycled and the remainder will be drawn off as a net hydrogen product gas stream. The reaction zone preferably comprises at least one radial flow reactor in which the catalyst gradually moves downward by gravity flow to allow the continuous replacement of used catalyst with catalyst having a higher activity. It is preferred that the reactants make at least two passes through a catalyst bed within the reaction zone. A detailed description of moving bed reactors of this type may be obtained by reference to U.S. Pat. Nos. 3,647,680; 3,706,536; 3,825,116; 3,839,196; 3,839,197; 3,854,887; 3,856,662; and 3,978,150.

The liquid stream withdrawn from the vapor-liquid separator is the effluent stream of the dehydrogenation reaction zone. This stream is passed into a fractionation system which preferably contains a single fractionation column referred to herein as the light ends stripping column. For MTBE production, this column is designed and operated to eliminate all ethane and lighter boiling components from the net dehydrogenation zone effluent stream. It may also separate some and possibly all of the propylene into the light ends stream removed from this zone. The propylene may result from the dehydrogenation of propane present in the feed stream to the process or may be formed during the undesired cracking of butanes, which also produces the other light ends removed from this zone.

The particular dehydrogenation conditions employed within the reaction zone may vary depending on such factors as the catalyst activity, feed carbon number, and the desired conversion. The reaction zone conditions normally employed for butane dehydrogenation include a temperature of from about 500° to 700° C., a pressure of from 0.5 to about 10 atmospheres and a liquid hourly space velocity of about 1 to 20. The preferred operating temperature will be within the range of from about 550° to 660° C., and the preferred operating pressure is about 0.5 to 2 atmospheres. The preferred butane dehydrogenation catalyst is comprised of a platinum group component, preferably platinum, a tin component and an alkali metal component with a porous inorganic carrier material. Other catalytic compositions may be used within this zone if desired. The preferred catalyst contains an alkali metal component chosen from cesium, rubidium, potassium, sodium, and lithium. The preferred alkali metal is normally chosen from lithium and potassium, with potassium being preferred for isobutane. Preferred dehydrogenation catalysts comprise an alkali metal and a halogen such as potassium and chlorine in addition to the tin and platinum group components. The preparation and use of dehydrogenation catalysts is well known to those skilled in the art and further details as to suitable catalyst compositions is available in patents and other standard references.

In order to increase the supply of isobutane available to the process and also to convert the nonreactive normal paraffins of the recycle stream the normal butanes of the recycle stream may, as previously described, be passed into a butane isomerization unit. As also previously described, the normal butanes are preferably first concentrated into an isomerization zone feed stream in a deisobutanizer column. The isomerization unit or zone comprises a reactor and auxiliary process equipment such as heaters, condensers, separatory vessels, etc. The isomerization unit preferably also contains a stripping column which eliminates light ends (hydrogen, methane, ethane) from the net effluent of the isomerization reactor. With the preferred catalyst, this stripping column will also remove volatile chloride compounds from the isomerization effluent.

The core of the operation of the isomerization unit is passage of the sidecut stream through a reactor maintained at butane isomerizationpromoting conditions including the presence of an acidic isomerization catalyst. This is normally a relatively low pressure operation performed at a pressure of from about 50 to 600 psig and at an elevated temperature as required by the activity of the catalyst. The average reactant temperature may be as high as 500° C., but is preferably between 100° and 320° C. It is normal practice to pass the butane through the reactor in admixture with between 1 and 10 moles of hydrogen per mole of butane to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired.

The effluent of the isomerization reactor is normally separated into a hydrogen-rich recycle gas which is returned to the reactor and an isomerate-containing liquid stream which is passed into the stripping column. It is within the scope of the inventive concept that this liquid stream may be further fractionated within the isomerization unit to allow the recycling of normal butanes and the achievement of higher conversion rates, but this is not preferred. The bottoms stream of the stripping column is the net hydrocarbon effluent of the isomerization unit and is a mixture of isobutane and normal butane. This stream should contain 50 mole percent isobutane. Preferably, this stream comprises 55 or 60 mole percent isobutane. The net hydrocarbon effluent of the isomerization unit is preferably charged into the deisobutanizer column which produces the feed stream to this unit. It could alternatively be passed directly into the dehydrogenation unit. Further details on the optional butane isomerization step may be obtained by referring to the previously cited references.

The preferred isomerization-promoting catalyst for use in the isomerization unit comprises a platinum group component and a halogen component supported by an inorganic oxide carrier. The preferred platinum group components are platinum and palladium or a mixture of platinum and palladium, with platinum being especially preferred. A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° to about 700° C. are usually satisfactory. The calcined composite is then reacted with a metal halide of the Friedel-Crafts type. Suitable metal halides include aluminum chloride, aluminum bromide, ferric chloride, zinc chloride, etc. Of these, aluminum chloride is particularly preferred.

To provide a more complete background for those embodiments in which the treated $C_4$ stream is passed into an alkylation zone, a brief description of the preferred form of an alkylation process is provided in the following paragraphs. As used herein, the term "alkylation reaction zone" is intended to indicate a sequence of processing equipment in which the entering reactants are contacted with an alkylation catalyst maintained at alkylationpromoting conditions including one or more reaction vessels and the required equipment for the separation and recovery of the resultant alkylate from process streams recirculated within the reaction zone. It is preferred that the alkylation reaction zone contains no fractionation columns other than that used for catalyst regeneration. The preferred alkylation reaction is the reaction between isobutane and normal butenes to produce high octane $C_8$ hydrocarbons useful as gasoline blending components. Other alkylation reactions can also be performed, but the alkylation zone will be described in terms of the preferred reaction.

The alkylation reaction is preferably promoted by the presence of a mineral acid-catalyst such as hydrofluoric acid, sulfuric acid or phosphoric acid with hydrofluoric acid being preferred. These acids are preferably maintained in a liquid phase containing a minimum of water to reduce corrosion problems. The maximum amount of water normally allowed in the acid is about 5 wt. %. When fresh acid is charged to a plant, it is normally very dry and contains about 0.5 wt. % water or less. The catalyst may also comprise a mixture of a mineral acid and a Friedel-Crafts metal halide promoter such as aluminum chloride, aluminum bromide, boron trifluoride, and other proton donors. A solid zeolitic catalyst could also be employed if desired.

Alkylation conditions in general include a pressure sufficient to maintain the hydrocarbons and acid in a liquid phase, with a general range being from about 20 to about 500 psig, and a more preferred range being from 100 to about 250 psig. It is preferred that the pressure within the reactantcatalyst contacting vessel is approximately 150 psig and esentially "floats" on the pressure maintained in the downstream fractionation zone. Although the desired alkylation reaction may be performed at temperatures from below −18° to about 90° C., it is preferred to operate the commercially prevalent isoparaffin-olefin alkylation process in the range of from about 10° to about 60° C., with 32° C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They could however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the monoolefin, the standard alkylation methods consist of either first admixing acid-free streams of olefin and isoparaffin to form a reactant mixture which is then admixed with the hydrofluoric acid, or an acid-free olefin stream is mixed with an acidcontaining isoparaffin stream. In either case, a large number of ventures or mixing nozzles are often utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into a fractionation column, which preferably operates as an isostripper column. This hydrocarbon phase will comprise mainly aklylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the standard reference materials.

The net hydrocarbonaceous effluent stream of the alkylation zone is preferably passed into the isostripper column of the motor fuel alkylation unit. The isostripper recovers the $C_8$ alkylate and other $C_5$-plus hydrocarbons as a net bottoms stream removed as the product of the process. When HF is used as the alkylation catalyst, the bottoms stream contains a small amount of isopentane produced in the alkylation zone. Some propane is also produced in a $C_4$ alkylation process. A representative set of operating conditions for this column includes an overhead vapor temperature of about 60° C. and an overhead pressure of approximately 150 psig. It may contain about 65 actual trays. Preferably, the alkylation zone effluent stream enters the isostripper column at an intermediate point. Sidecut streams are preferably removed above and below the feed point. The upper sidecut carries isobutane which has passed through the alkylation zone. Preferably, this isobutane-rich stream is recycled into the alkylation zone. The lower sidecut stream will normally be rich in normal butane and is withdrawn from the alkylation unit. Since it is a lower sidecut stream, it will contain some product alkylate.

Propane, including that which is present in the feed stream to the process, will enter the isostripper as part of the alkylation zone effluent stream. The propane is concentrated into the net overhead vapor of the isostripper. The overhead of the isostripper column will also contain HF and isobutane. This net overhead is preferably passed into a second column referred to in the art as a depropanizer in which the isobutane is recovered as a bottoms product. This isobutane is preferably recycled back to the alkylation zone by admixture into the upper sidecut stream of the isostripper. If there is an excess of isobutane fed to the alkylation unit, this bottoms stream is a good source of high purity isobutane and may be withdrawn from the alkylation zone after being alumina treated. The net overhead of the depropanizer comprises HF and propane and is preferably sent to a third column in which HF is stripped off as an overhead product. The HF may be returned to the alkylation zone and the propane is removed as a net bottoms product and transferred to suitable storage facilities after alumina treatment.

I claim as my invention:

1. A process for the production of an ether which comprises the steps of:
   (a) passing a first process stream comprising a feed isoparaffin through a catalytic dehydrogenation reaction zone and thereby producing a reaction zone effluent stream comprising the isoparaffin and a corresponding isoolefin;
   (b) passing the reaction zone effluent stream and a hereinafter characterized second process stream into a stripping column and producing a stripping column bottoms stream comprising the isoparaffin, oxygencontaining hydrocarbonaceous compounds, and the corresponding isoolefin;
   (c) passing the stripping column bottoms stream and a feed stream comprising an alcohol into an etherification zone maintained at etherification conditions, and withdrawing from the etherification zone a product stream comprising an ether and a hydrocarbonaceous third process stream comprising the isoparaffin and oxygen-containing hydrocarbonaceous compounds;
   (d) removing oxygen-containing hydrocarbonaceous compounds from the third process stream by contacting the third process stream with a selective sorbent at sorption-promoting conditions in a sorption zone and thereby producing a treated process stream which comprises the isoparaffin and is substantially free of oxygen-containing hydrocarbonaceous compounds;
   (e) removing at least a first portion of the treated process stream from the process; and,
   (f) regenerating sorbent in the sorption zone by a regeneration procedure which comprises contacting sorbent present in the sorption zone with a regeneration stream comprising a regenerent hydrocarbon having the same number of carbon atoms per molecule as the feed isoparaffin at regeneration-promoting conditions including a temperature above 250° F. to produce the previously referred to second process stream, which comprises the regenerated hydrocarbon and oxygen-containing hydrocarbonaceous compounds.

2. The process of claim 1 further characterized in that the feed isoparaffin is isobutane.

3. The process of claim 2 further characterized in that the alcohol is ethanol.

4. The process of claim 2 further characterized in that the alcohol is methanol and the ether is methyl tertiary butyl ether.

5. The process of claim 4 further characterized in that the third process stream comprises dimethyl ether and methyl tertiary butyl ether when withdrawn from the etherification zone.

6. The process of claim 5 further characterized in that the third process stream comprises methanol and isobutane.

7. The process of claim 2 further characterized in that the regenerant hydrocarbon is isobutane or normal butane and in that the regeneration stream is prepared in a hydrocarbon conversion zone other than the dehydrogenation zone or the etherification zone.

* * * * *